United States Patent [19]

Moll

[11] Patent Number: 5,305,121
[45] Date of Patent: Apr. 19, 1994

[54] STEREOSCOPIC ENDOSCOPE SYSTEM

[75] Inventor: Frederic H. Moll, San Francisco, Calif.

[73] Assignee: Origin Medsystems, Inc., Menlo Park, Calif.

[21] Appl. No.: 895,128

[22] Filed: Jun. 8, 1992

[51] Int. Cl.$^5$ .................. A61B 1/04; H04N 13/02
[52] U.S. Cl. ................................ 348/45; 348/65
[58] Field of Search ............ 358/98, 88; 128/6; H04N 13/02

[56] References Cited

U.S. PATENT DOCUMENTS

| | | | |
|---|---|---|---|
| 4,862,873 | 9/1989 | Yajima | 128/6 |
| 4,873,572 | 10/1989 | Miyazaki | 358/98 |
| 4,920,413 | 4/1990 | Nakamura | 358/98 |
| 4,935,810 | 6/1990 | Nonami | 358/98 |
| 4,994,079 | 2/1991 | Genese | 128/6 |
| 5,074,642 | 12/1991 | Hicks | 385/116 |
| 5,109,276 | 4/1992 | Nudelman | 358/88 |
| 5,121,740 | 6/1992 | Uram | 128/6 |

Primary Examiner—Tommy P. Chin
Assistant Examiner—Bryan S. Tung
Attorney, Agent, or Firm—Heller, Ehrman, White & McAuliffe

[57] ABSTRACT

An endoscope for stereoscopic viewing of surgical procedures, consisting of two solid-state cameras and a bundle of illuminating optic fibers. The width of the optic fiber bundle is approximately equal to that of the endoscope thereby maximizing the amount of light which the bundle can provide. The viewing cameras can be separated to a distance greater than the width of the sheath for enhanced depth perception and greater light delivery, and withdrawn into the sheath for insertion and withdrawal of the endoscope from the surgical cavity. The orientation of the cameras can be controlled to provide off-axis viewing.

21 Claims, 3 Drawing Sheets

STEREOSCOPIC ENDOSCOPE SYSTEM

FIELD OF THE INVENTION

This invention relates to surgical instruments, and in particular to endoscopic surgical instruments. Specifically, this invention relates to a system for stereoscopic viewing of endoscopic medical procedures.

BACKGROUND OF THE INVENTION

The last decade has seen dramatic advances in the field of endoscopic instrumentation, and the application of endoscopic techniques to a growing number of surgical procedures. The benefits—reduced pain and discomfort, shortened recovery time and better cosmetic results—insure that endoscopic surgery will continue to be a rapidly developing and widely applied technique.

Endoscopic surgery is performed with elongated instruments inserted through small holes in the skin, and is viewed through an endoscope. The image acquired by the endoscope is generally displayed on a video monitor. Endoscopic operations require more mental and physical dexterity than corresponding traditional surgical techniques. Because of these additional difficulties it is important to provide endoscopic instruments which are easy and convenient to use, and viewing systems which are as informative as possible.

Traditionally, endoscopes only utilize a single lens train and so only provide monoscopic viewing of surgical procedures. Since monoscopic views provide no depth information the surgeon must rely on foreshortening effects or tactile clues to determine depth relative to the viewing lens.

SUMMARY AND OBJECTS OF THE INVENTION

The present invention is directed to a method and apparatus for improved viewing of endoscopic procedures. The endoscope of the present invention utilizes two solid state cameras to provide a stereoscopic view. The orientation of the cameras can be controlled at the extracorporeal end of the endoscope. The distance between the cameras can be contracted to a width less than the diameter of the cannula for insertion and extraction of the endoscope, and when positioned in the surgical cavity the cameras can be separated to a distance greater than the width of the cannula. A bundle of optic fibers provides illumination to the surgical cavity. Preferably, the width of the bundle is approximately equal to that of the endoscope thereby maximizing the amount of light the bundle can provide.

Therefore, an object of the present invention is to provide an endoscope that provides stereoscopic viewing.

Another object of the present invention is to provide an endoscope which maximizes the illumination provided to the surgical cavity.

Another object of the present invention is to provide a stereoscopic endoscope where the orientation of the cameras can be adjusted.

Another object of the present invention is to provide a stereoscopic endoscope which allows off-axis viewing.

Another object of the present invention is to provide an endoscope which by separating two separate cameras at the distal end of the endoscope to a width greater than that of the cannula provides a method of maximizing image quality and light delivery in endoscopic procedures which are carried out in large body cavities.

Further objects and advantages of this invention will become apparent upon review of the following specification and claims.

DESCRIPTION OF THE PREFERRED EMBODIMENTS

Figure 1:
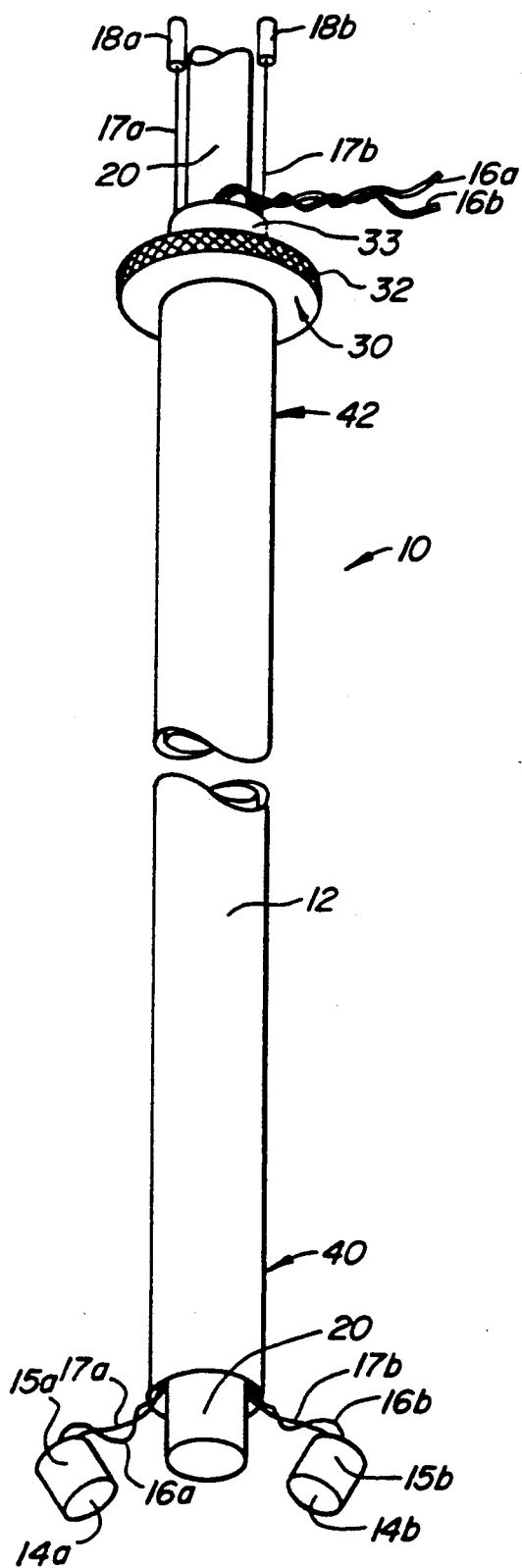
FIG. 1 is a view of an embodiment of an endoscope of the present invention with the cameras and illumination bundle extending past the intracorporeal end of the sheath, and the cameras focused on a region along the longitudinal axis of the sheath.

FIG. 1 shows a first embodiment of the endoscope 10 of the present invention. The endoscope 10 has a left support rod 17a, a right support rod 17b, a left image signal wire 16a, a right image signal wire 16b, and a fiber optic illumination bundle 20 extending from both the intracorporeal end 40 and the extracorporeal end 42 of the sheath 12. The illumination bundle 20 has a width only slightly less than the interior width of the sheath 12. The illumination bundle 20 may be bendable so as to enable the operator to direct light towards the viewed region, or may have a diffusing lens (not shown) at the intracorporeal end thereof to scatter light transmitted by the illumination bundle 20 over a wide solid angle. Typically, sheath 12 has a length of approximately 250 cm, and a width of approximately 10 mm. A left camera 15a and a right camera 15b are mounted at the intracorporeal ends of rods 17a and 17b and electrically connected to signal wires 16a and 16b, respectively. The cameras 15a and 15b have lenses 14a and 14b for focusing images on image planes of image transducers (not shown) in the interiors of the cameras 15a and 15b, respectively.

The image transducers in the cameras 15a and 15b are preferably solid-state image sensors, and most preferably image sensors using charge-coupled devices (CCDs). In FIG. 1 the cameras 15a and 15b lie substantially in the same plane as the illumination bundle 20 and the region of intersection of the views of the two cameras 15a and 15b lies along the longitudinal axis of the illumination bundle 20.

Figures 5, 6:
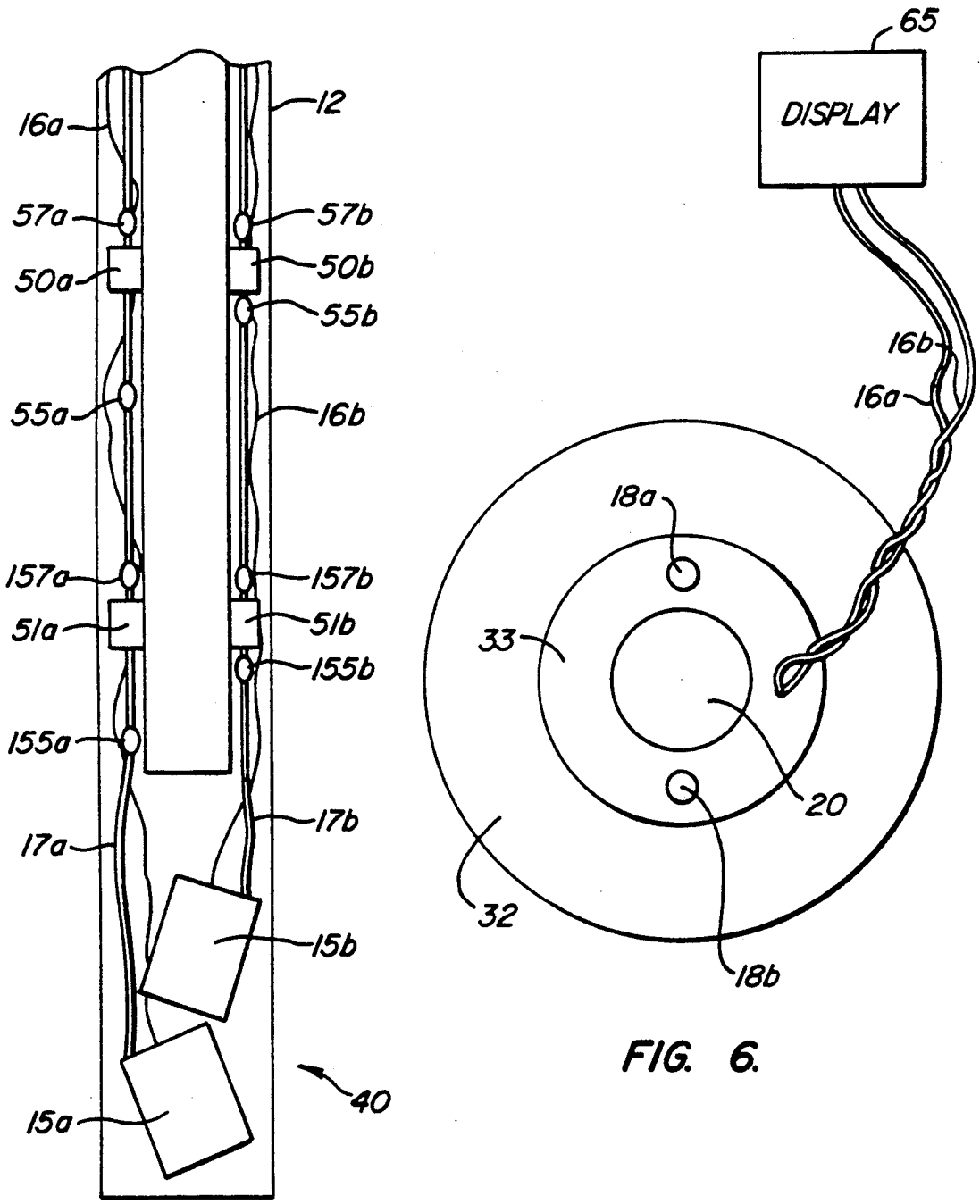
FIG. 5 is a cross-sectional view of the intracorporeal end of the endoscope of FIG. 3.
FIG. 6 is a top view of the embodiment of FIG. 1.

The extracorporeal end 42 of the sheath 12 is fitted with a plug 30. The plug 30 has a laterally extending grip section 32 with a textured lateral circumference for ease of gripping, a shaft section 34 (shown in FIG. 3) extending downwards from the grip section 32, and a head section 33. The shaft 34 is cylindrical with an outside diameter slightly less than the inside diameter of the sheath 12 thereby allowing the shaft 34 to slide into and out of the sheath 12. The signal wires 16a and 16b, the support rods 17a and 17b and the illumination bundle 20 pass through the shaft 34, grip section 32 and head 33 of the plug 30. Orientation knobs 18a and 18b are mounted at the extracorporeal ends of support rods 17a and 17b, respectively. As shown in FIG. 6, the illumination bundle 20 passes through the center of the head 33, and the orientation knobs 18a and 18b are located on opposite sides of the illumination bundle 20. The signal wires 16a and 16b pass through a bore in the head 33 which is located 90° from both orientation knobs 18a and 18b, and are directed to a display mean 65.

Figure 2:
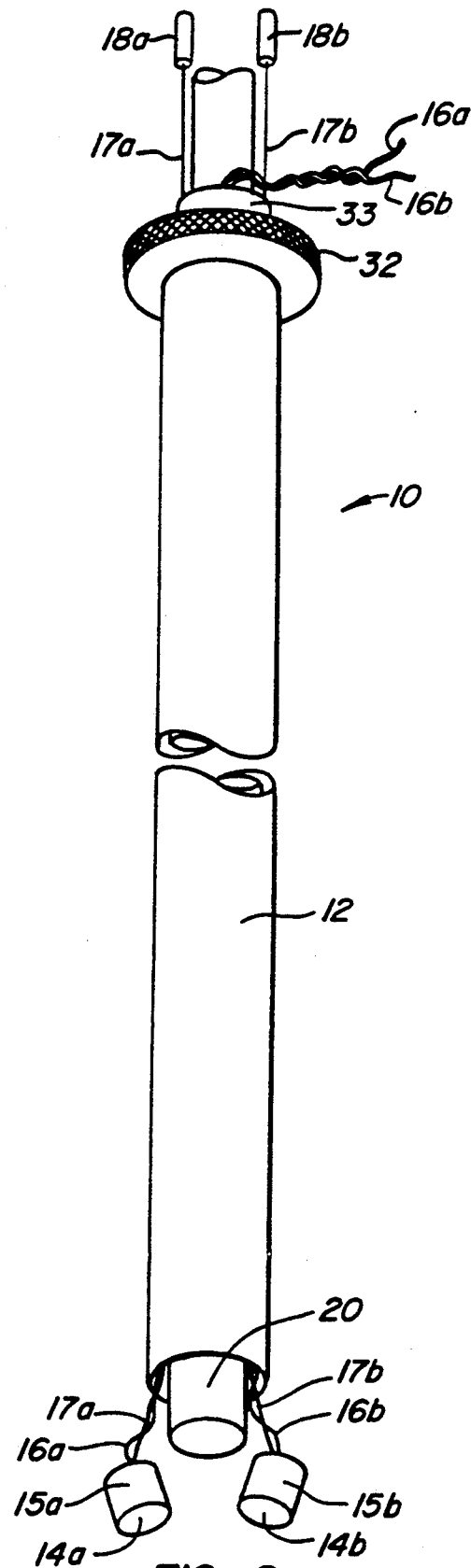
FIG. 2 is a view of the embodiment of FIG. 1 having the cameras focused on a region off the longitudinal axis of the sheath.
Figure 4:
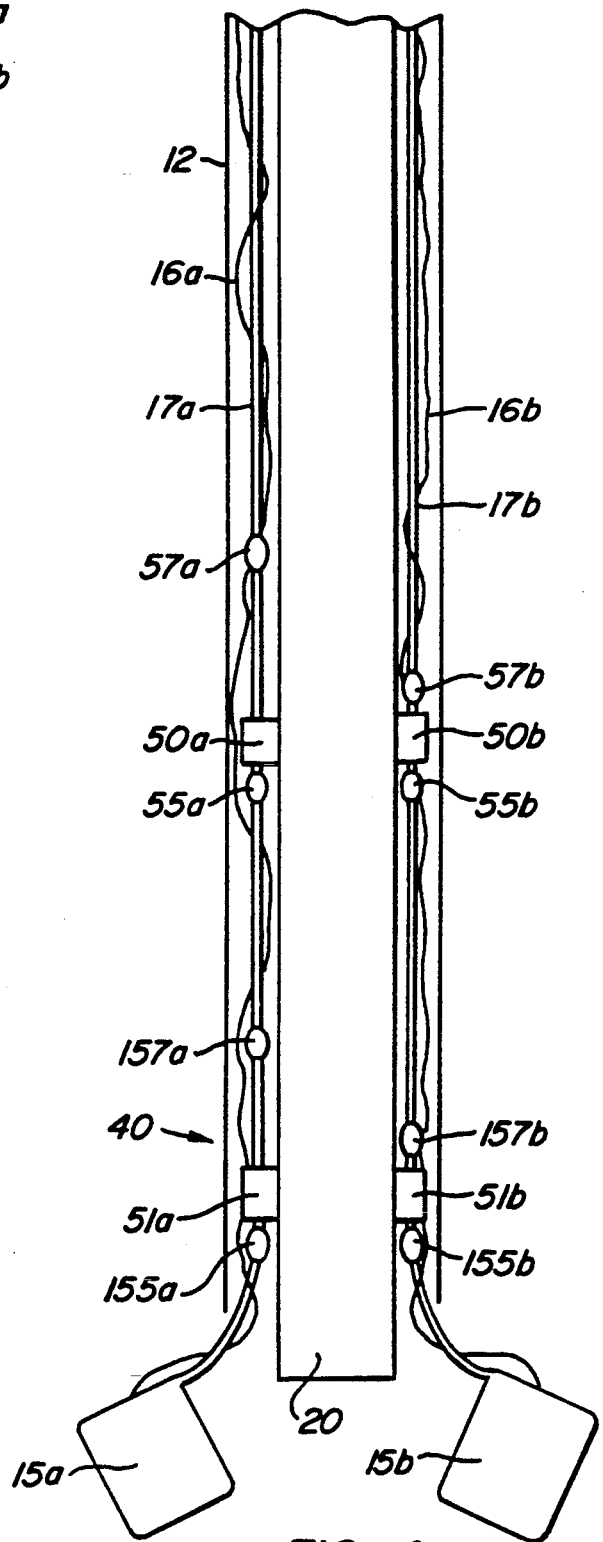
FIG. 4 is a cross-sectional view of the intracorporeal end of the endoscope of FIG. 1.

Support rods 17a and 17b have shape memory, and in the preferred embodiment are made of spring steel or nitenol (a shape memory metal composed of a nickel-titanium alloy). When unstressed the intracorporeal ends of support rods 17a and 17b are arced as shown in FIGS. 1, 2 and 4. When the intracorporeal ends of the support rods 17a and 17b are outside the sheath 12, the rods 17a and 17b support the cameras 15a and 15b off the longitudinal axis of the sheath 12 and orient the fields of view of the cameras 15a and 15b towards the longitudinal axis of the endoscope 10. The support rods 17a and 17b have sufficient stiffness and sturdiness to deploy in a highly consistent and controlled manner. The orientations of the cameras 15a and 15b are therefore relatively unsusceptible to the environment and, for instance, contact of a camera 15a or 15b with body tissue will not reorient the camera 15a or 15b.

Whereas the illumination bundle 20 is secured to the head 33 by an adhesive or by friction fit between these elements, the support rods 17a and 17b are free to rotate. Rotation of orientation knobs 18a and 18b induces rotation of the support rods 17a and 17b and displacements of the cameras 15a and 15b, respectively. By rotating the left orientation knob 18a to the left and the right orientation knob 18b to the right the cameras 15a and 15b are displaced into the plane of FIG. 1 to produce the configuration of FIG. 2. In FIG. 2 the cameras 15a and 15b do not lie in the same plane as the illumination bundle 20, and the intersection of the regions viewed by cameras 15a and 15b lies off the longitudinal axis of the illumination bundle 20. The degree to which the stereoscopic view provided by cameras 15a and 15b deviates from the longitudinal axis of the bundle 20 varies continuously with the rotation of orientation knobs 18a and 18b. Depending on the displacement of the viewing region of cameras 15a and 15b from the longitudinal axis of the illumination bundle 20, the illumination bundle can be made steerable to follow the changing axis of the imaging cameras 15a and 15b, or a diffusing lens may be attached at the end of the illumination bundle 20 to provide adequate light intensity on the viewing region. It should be noted however that though a diffusing lens increases the area which is illuminated, the light intensity incident on the illuminated area is lessened.

FIG. 4 shows a cross-sectional view of the intracorporeal end of the endoscope 10 with the cameras 15a and 15b protruding from the intracorporeal end 40 of the sheath 12. Lower guides 51a and 51b protrude from opposite sides of the illumination bundle 20 near the intracorporeal end thereof. Upper guides 50a and 50b protrude from opposite sides of the illumination bundle 20 to the extracorporeal side of the lower guides 51a and 51b. Support rod 17a passes through bores (not shown) in the upper guide 50a and the lower guide 51a. Similarly, support rod 17b passes through bores (not shown) in the upper guide 50b and the lower guide 51b. The bores in the guides 50a, 50b, 51a and 51b have a width greater than the widths of the support rods 17a and 17b, and therefore allow the support rods 17a and 17b to be rotated about their longitudinal axes.

Beads 155b and 157b mounted on the right support rod 17b closely bracket lower guide 51b, and similarly beads 55b and 57b mounted on the right support rod 17b closely bracket upper guide 50b. The beads 55b, 155b, 57b and 57b have a width greater than the width of the bore through right upper and lower guides 50b and 51b thereby preventing longitudinal displacement of the right support rod 17b. Beads 155a and 157a mounted on the left support rod 17a are separated by a distance approximately equal to the width of the right camera 15b plus the length of the lower left guides 51a. Similarly, beads 55a and 57a mounted on the left support rod 17a are separated by a distance approximately equal to the width of the right camera 15b plus the length of the upper left guide 50a. The beads 55a, 155a, 57a and 57a have a width greater than the width of the bore through left upper and lower guides 50a and 51a thereby allowing the longitudinal displacement of the left support rod 17a by a distance approximately equal to the width of a camera 15a or 15b.

Figure 3:
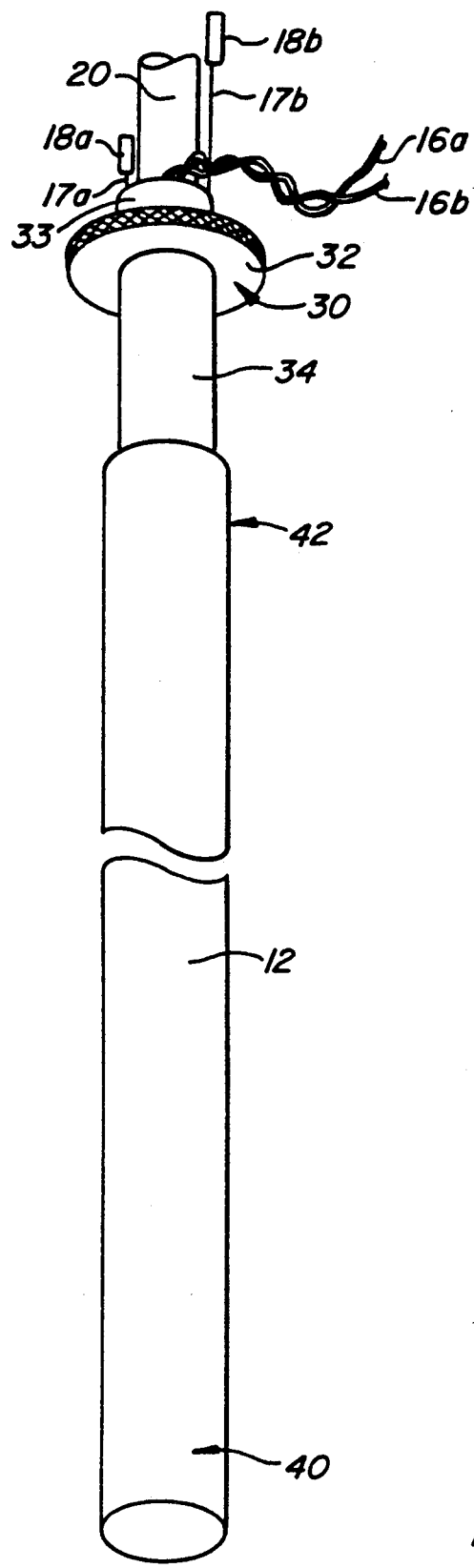
FIG. 3 is a view of the embodiment of FIG. 1 having the cameras and illumination bundle withdrawn into the sheath.

Upon displacement of the plug 30 away from the extracorporeal end 42 of the sheath 12 the upper and lower right guides 50b and 51b engage the beads 57b and 157b, respectively, so the right support rod 17a is displaced by the same distance as the plug 30. The intracorporeal end of the sheath 12 exerts a force on the right support rod 17b which bends the rod 17b and forces the right camera 15b to a position directly below the extracorporeal end of the illumination bundle 20. After the plug 30 has been displaced by a distance approximately equal to the width of the right camera 15b the left guides 50a and 51a engage the beads 57a and 157a, respectively, and begin to retract the left camera 15a into the sheath 12. The intracorporeal end of the sheath 12 exerts a force on the left support rod 17a which bends the rod 17a and forces the left camera 15a to a position directly below the right camera 15b. FIG. 5 depicts a cross-sectional view of the intracorporeal end 40 of the endoscope 10 with the cameras 15a and 15b retracted into the sheath 12, and FIG. 3 shows an exterior view of this configuration.

In the preferred embodiment the grip section 32, the shaft 34 and the head 33 of the plug 30, the sheath 12, the exterior casings of the cameras 15a and 15b, the guides 50a, 50b, 51a and 51b, the beads 55a, 55b, 155a, 155b, 57a, 57b, 157a, 157b, and the orientation knobs 18a and 18b are made of a hard plastic, e.g. polyvinyl chloride. The cameras 15a and 15b may be solid-state cameras which utilize charge transfer elements, such as CCD cameras.

Use of the endoscope 10 of the present invention is convenient and straightforward. Access to the surgical region is obtained by puncturing the skin and other selected intervening tissues with a trocar. The cannula is left in place during surgery to provide a conduit for the endoscope. The sheath 12 has a diameter slightly less than that of the cannula of the trocar allowing its insertion into the cannula once the cameras 15a and 15b have been withdrawn into the sheath 12 by pulling the plug 30 away from the sheath 12. The intracorporeal end 40 of the endoscope 10 is then inserted into the cannula. The sheath 12 may be engaged by a seal mechanism on the trocar to prevent intracorporeal gases and fluids from escaping through the cannula during surgery. Other punctures are made in other locations for insertion of other endoscopic instruments.

The endoscope is connected to extracorporeal support equipment. Light from a light source focused onto the extracorporeal end of the illumination bundle 20 is channeled to the intracorporeal end of the fibers in the bundle 20 and emitted, thereby illuminating the surgical cavity. It will be realized that modifications may be made which are within the spirit and scope of the invention. For example, a sufficiently flexible illumination bundle may be bent with mechanical or electrical steering controls so as to allow the light to be directed towards the area viewed by the cameras 15a and 15b. Or, a diffusing lens may be attached at the intracorporeal end of the illumination bundle 20 to scatter the light over a larger solid angle thereby illuminating off-axis regions of the surgical cavity.

Upon insertion of the endoscope 10 into the surgical cavity the cameras 15a and 15b are extruded from the sheath 12 by pushing the shaft 34 of the plug 30 into the sheath 12. This forces the illumination bundle 20 and the upper and lower right guides 50b and 51b towards the intracorporeal end 40 of the sheath 12. The upper and lower right guides 50b and 51b engage the beads 55b and 155b, respectively, on the right support rod 17b forcing the right support rod 17b and the attached right camera 15b towards the intracorporeal end 40 of the sheath 12. The right camera 15b then comes into contact with the left camera 15a thereby also pushing that camera 15a and the attached support rod 17a out of the extracorporeal end 40 of the sheath 12. As the cameras 15a and 15b and intracorporeal ends of the support rods 17a and 17b extend past the intracorporeal end of the sheath 12, intracorporeal end portions of the support rods 17a and 17b become unstressed and arc away from the longitudinal axis of the sheath, thereby separating cameras 15a and 15b.

If an off-axis region is to be viewed the displacement of the viewing region from the longitudinal axis of the endoscope 10 is controlled by the rotation of orientation knobs 18a and 18b which controls the orientation of the cameras 15a and 15b as described above. The azimuthal angle of the viewing region is controlled by rotation of the entire endoscope 10 about its longitudinal axis. For viewing a region at a large angle from the longitudinal axis of the endoscope 10 it may be desirable to steer the intracorporeal end of the illumination bundle 20, for example, by bending the bundle, or to cap the illumination bundle 20 with a diffusing lens to provide light to off-axis regions.

The maximum amount of light which may be transmitted by a bundle of optic fibers is proportional to the cross-sectional area of the bundle. The illumination bundle 20 can provide a relatively large light intensity since the bundle 20 has a width only slightly less than the interior width of the sheath 12. The cameras 15a and 15b generate electronic signals which are channeled to the extracorporeal end 42 of the endoscope 10 by signal wires 16a and 16b. Image signals generated by the cameras 15a and 15b are processed at a two-channel processor (not shown) for color enhancement and noise reduction. The processed image signals are displayed on a video monitor display means 65. The video monitor display means 65 can be in the form of viewing goggles which display two adjacent video images. When the goggles are worn one video display is viewed by each eye thereby providing a stereoscopic view of the images. Alternatively, the video images may still provide a stereoscopic effect while displayed on a single video monitor, by alternating the images from the two cameras 15a and 15b. A process for alternating images is described in *Defense Science and Engineering*, August 1986, pp. 30–31, incorporated by reference herein. Typically the images are alternately displayed at a rate of 4 to 30 times per second.

In an alternate embodiment, the sheath 12 is not present in the endoscope 10. The elimination of the sheath 12 provides additional space for the other components of the endoscope 10. To insert the endoscope 10 into the cannula the the supporting rods 17a and 17b are bent so the cameras 15a and 15b lie on-axis. Once the endoscope is positioned inside the cannula the operation of the alternate embodiment is substantially as described above. For instance, the cannula of the trocar functions as the sheath 12 to restrain the cameras 15a and 15b to on-axis positions while the cameras 15a and 15b lie within the cannula and once the cameras 15a and 15b are extruded past the intracorporeal end of the cannula they separate so as to provide stereoscopic viewing outside of the light path from the illumination bundle 20.

From the foregoing description it can therefore be seen that the present invention provides an improved endoscope for stereoscopic viewing of endoscopic surgical procedures. The endoscope of the present invention allows for the adjustment of the orientation of the viewing cameras. Although the specifics of the preferred embodiments have been described in detail for clarity and understanding many other variations are within the skill of those of ordinary skill in the art. For instance, the sheath and casing of the illumination bundle may be flexible so that the endoscope may be inserted into body cavities by non-surgical methods; mechanisms for cleaning the lenses of the cameras or the intracorporeal end of the illumination bundle may be installed; the orientation of the cameras may be adjusted by other mechanisms; the retraction and extrusion of the cameras and the illumination bundle may be implemented by other mechanisms; illumination may be provided by an electric light; the separation between the cameras may be adjustable; each lens may be replaced by series of lenses to improve the magnification or focusability of the endoscope; the endoscope may be adapted for seating of other surgical instruments such as a ligation loop or forceps; the illumination bundle may retain a fixed position relative to the sheath while the cameras 15a and 15b are retracted and extruded; or the cameras may fit side by side inside the sheath rather than in a staggered configuration. Therefore, the scope of the present invention should not be determined by the details of the specification but rather by the following claims.

What is claimed is:

1. An endoscope for providing a view of a surgical cavity on a display means, comprising
   a first lens means for focusing a first image of a viewed region of said surgical cavity onto a first image plane;
   a second lens means for focusing a second image of said viewed region of said surgical cavity onto a second image plane;
   a first means for transmitting said first image to said display means;
   a second means for transmitting said second image to said display means, said display means providing a stereoscopic display of said region of said surgical cavity, an elongated housing, said elongated housing having a longitudinal axis, an extracorporeal end, an intracorporeal end, and an interior width, and a means for moving said first and second lens means between a retracted configuration wherein said first and second lens means are located inside said elongated housing and an extruded configuration wherein said first and second lens means are located outside said elongated housing and separated by a distance greater than said interior width of said elongated housing.

2. The endoscope of claim 1 further including a first transducing means located near said first image plane for generating a first electrical signal corresponding to said first image, and a second transducing means located near said second image plane for generating a second electrical signal corresponding to said second image.

3. The endoscope of claim 2 wherein said first means for transmitting said first image to said display means comprises at least one wire and said second means for transmitting said second image to said display means comprises at least one wire.

4. The endoscope of claim 2 further including a means for illuminating said region of said surgical cavity.

5. The endoscope of claim 4 wherein said means for illuminating said surgical region comprises optic fibers.

6. The endoscope of claim 5 wherein said optic fibers pass through said elongated housing.

7. The endoscope of claim 6 wherein said optic fibers comprise a bundle having a width greater than half said interior width of said elongated housing.

8. The endoscope of claim 6 wherein said optic fibers comprise a bundle having a width greater than said interior width of said elongated housing less a width of said first transducing means along a direction transverse to said longitudinal axis.

9. The endoscope of claim 6 wherein said optic fibers comprise a bundle having a width greater than said interior width of said elongated housing less widths of said first and second transducing means along a direction transverse to said longitudinal axis.

10. The endoscope of claim 4 further including means for orienting said first and second lenses between a first configuration wherein said viewed region is along said longitudinal axis and a second configuration wherein said viewed region is off said longitudinal axis.

11. An endoscope for insertion through an elongated cannula to provide a view of a surgical cavity on a display means, said elongated cannula having a longitudinal axis, an extracorporeal end, an intracorporeal end, and an interior width, comprising a first lens means for focusing a first image of a viewed region of said surgical cavity onto a first image plane;

a second lens means for focusing a second image of said viewed region of said surgical cavity onto a second image plane;

a first means for transmitting said first image to said display means;

a second means for transmitting said second image to said display means, said display means providing a stereoscopic display of said viewed region of said surgical cavity, and a means for moving said first and second lens means between a retracted configuration wherein said first and second lens means are located inside said elongated cannula and an extruded configuration wherein said first and second lens means are located outside said elongated cannula and separated by a distance greater than said interior width of said elongated cannula.

12. The endoscope of claim 11 further including a first transducing means located near said first image plane for generating a first electrical signal corresponding to said first image, and a second transducing means located near said second image plane for generating a second electrical signal corresponding to said second image.

13. The endoscope of claim 12 wherein said first means for transmitting said first image to said display means comprises at least one wire and said second means for transmitting said second image to said display means comprises at least one wire.

14. The endoscope of claim 12 further including a means for illuminating said viewed region of said surgical cavity.

15. The endoscope of claim 14 wherein said means for illuminating said viewed region of said surgical cavity comprises optic fibers.

16. The endoscope of claim 15 wherein said optic fibers comprise a bundle having a width greater than half said interior width of said elongated cannula.

17. The endoscope of claim 15 wherein said optic fibers comprise a bundle having a width greater than said interior width of said elongated cannula less a width of said first transducing means along a direction transverse to said longitudinal axis.

18. The endoscope of claim 15 wherein said optic fibers comprise a bundle having a width greater than said interior width of said elongated cannula less widths of the first and second transducing means along a direction transverse to said longitudinal axis.

19. The endoscope of claim 14 further including means for orienting said first and second lenses between a first configuration wherein said viewed region is along said longitudinal axis and a second configuration wherein said viewed region is off said longitudinal axis.

20. The endoscope of claim 1 for insertion through a cannula to provide a stereoscopic display of said surgical cavity and wherein said elongated housing includes a first interior cross-sectional area, said endoscope further comprising:

a first transducing means located near said first image plane for generating a first electrical signal corresponding to said first image, said first transducing means having a second cross-sectional area perpendicular to said longitudinal axis;

a second transducing means located near said second image plane for generating a second electrical signal corresponding to said second image, said second transducing means having a third cross-sectional area perpendicular to said longitudinal axis; and optic fibers having an intracorporeal end and passing through said housing, said intracorporeal end of said optic fibers having a fourth cross-sectional area greater than said first interior cross-sectional area less said second and third cross-sectional areas, whereby said optic fibers provide increased illumination to said surgical cavity.

21. The endoscope of claim 20 wherein said fourth cross-sectional area is greater than said first interior cross-sectional area less said second cross-sectional area, whereby said optic fibers provide increased illumination to said surgical cavity.

* * * * *

UNITED STATES PATENT AND TRADEMARK OFFICE
CERTIFICATE OF CORRECTION

PATENT NO. : 5,305,121
DATED : April 19, 1994
INVENTOR(S) : Frederic H. Moll

It is certified that error appears in the above-indentified patent and that said Letters Patent is hereby corrected as shown below:

Column 4, line 7, "57b and 57b" should be --57b and 157b--.

Column 4, line 17, "57a and 57a" should be --57a and 157a--.

Signed and Sealed this

Thirtieth Day of August, 1994

*Attest:*

BRUCE LEHMAN

*Attesting Officer*     *Commissioner of Patents and Trademarks*